United States Patent
Wham et al.

(10) Patent No.: US 7,300,435 B2
(45) Date of Patent: Nov. 27, 2007

(54) AUTOMATIC CONTROL SYSTEM FOR AN ELECTROSURGICAL GENERATOR

(75) Inventors: Robert H. Wham, Boulder, CO (US); Thomas A. Sturm, Erie, CO (US)

(73) Assignee: Sherwood Services Ag, Schaffhausen (CH)

( * ) Notice: Subject to any disclaimer, the term of this patent is extended or adjusted under 35 U.S.C. 154(b) by 768 days.

(21) Appl. No.: 10/719,305

(22) Filed: Nov. 21, 2003

(65) Prior Publication Data

US 2005/0113819 A1    May 26, 2005

(51) Int. Cl.
*A61B 18/18*    (2006.01)
(52) U.S. Cl. .......................................... 606/34; 606/32
(58) Field of Classification Search ............. 606/32–35
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 2,982,881 A | 5/1961 | Reich |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Glannamore |
| 3,515,943 A | 6/1970 | Warrington |

(Continued)

FOREIGN PATENT DOCUMENTS

DE          179607          3/1905

(Continued)

OTHER PUBLICATIONS

Ogden "Goertzel Alternative to the Fourier Transform" Jun. 1993, pp. 485-487, Electronics World; Reed Business Publishing, Sutton, Surrey, GB vol. 99, No. 1687.*

(Continued)

*Primary Examiner*—Michael Peffley (57) ABSTRACT

An automatic control system for an electrosurgical generator is herein disclosed. The automatic control system includes voltage and current sensing circuits, a processing circuit, an output determining circuit, and a control circuit. Samples of the voltage and current outputs are supplied to the processing circuit and the output determining circuit to generate an output signal. The output signal is compared to a reference signal to generate a feedback signal for controlling a drive circuit.

13 Claims, 1 Drawing Sheet

U.S. PATENT DOCUMENTS

| | | |
|---|---|---|
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Biertein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,437,464 A | 3/1984 | Crow |
| 4,438,766 A | 3/1984 | Bowers |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,590,934 A | 5/1986 | Malis et al. |
| 4,608,977 A | 9/1986 | Brown |
| 4,630,218 A | 12/1986 | Hurley |
| 4,632,109 A | 12/1986 | Patterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,712,559 A | 12/1987 | Turner |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,788,634 A | 11/1988 | Schlecht et al. |
| 4,805,621 A | 2/1989 | Heinze et al. |
| 4,818,954 A | 4/1989 | Flachenecker et al. |
| 4,827,911 A | 5/1989 | Broadwin et al. |
| 4,827,927 A | 5/1989 | Newton |
| 4,832,024 A | 5/1989 | Boussignac et al. |
| 4,848,335 A | 7/1989 | Manes |
| 4,848,355 A | 7/1989 | Nakamura et al. |
| 4,860,745 A | 8/1989 | Farin et al. |
| 4,862,889 A | 9/1989 | Feucht |
| 4,880,719 A | 11/1989 | Murofushi et al. |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,961,047 A | 10/1990 | Carder |
| 4,961,435 A | 10/1990 | Kitagawa et al. |

| Patent No. | Date | Inventor |
|---|---|---|
| 4,966,597 A | 10/1990 | Cosman |
| RE33,420 E | 11/1990 | Sussman |
| 4,969,885 A | 11/1990 | Farin |
| 4,993,430 A | 2/1991 | Shimoyama et al. |
| 4,995,877 A | 2/1991 | Ams et al. |
| 5,015,227 A | 5/1991 | Broadwin et al. |
| 5,019,176 A | 5/1991 | Brandhorst, Jr. |
| 5,029,588 A | 7/1991 | Yock et al. |
| 5,087,257 A | 2/1992 | Farin |
| 5,103,804 A | 4/1992 | Abele et al. |
| 5,108,389 A | 4/1992 | Cosmescu |
| 5,108,391 A | 4/1992 | Flachenecker |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,162,217 A | 11/1992 | Hartman |
| 5,167,658 A | 12/1992 | Ensslin |
| 5,190,517 A | 3/1993 | Zieve et al. |
| 5,196,008 A | 3/1993 | Kuenecke |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,249,121 A | 9/1993 | Baum et al. |
| RE34,432 E | 11/1993 | Bertrand |
| 5,267,994 A | 12/1993 | Gentelia et al. |
| 5,267,997 A | 12/1993 | Farin |
| 5,281,213 A | 1/1994 | Milder et al. |
| 5,300,068 A | 4/1994 | Rosar et al. |
| 5,300,070 A | 4/1994 | Gentelia |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,193 A | 8/1994 | Nardella |
| 5,341,807 A | 8/1994 | Nardella |
| 5,342,356 A | 8/1994 | Ellman |
| 5,342,357 A | 8/1994 | Nardella |
| 5,342,409 A | 8/1994 | Mullett |
| 5,348,554 A | 9/1994 | Imran et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A * | 12/1994 | Klicek et al. .................. 606/35 |
| 5,383,874 A | 1/1995 | Jackson |
| 5,383,876 A | 1/1995 | Nardella |
| 5,383,917 A | 1/1995 | Desai et al. |
| 5,385,148 A | 1/1995 | Lesh et al. |
| 5,396,062 A | 3/1995 | Eisentraut et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,006 A | 4/1995 | Buchholtz et al. |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,423,808 A | 6/1995 | Edwards et al. |
| 5,423,809 A | 6/1995 | Klicek |
| 5,423,810 A | 6/1995 | Goble et al. |
| 5,430,434 A | 7/1995 | Lederer et al. |
| 5,432,459 A | 7/1995 | Thompson |
| 5,433,739 A | 7/1995 | Sluijter et al. |
| 5,434,398 A | 7/1995 | Goldberg |
| 5,436,566 A | 7/1995 | Thompson |
| 5,438,302 A | 8/1995 | Goble |
| 5,443,463 A | 8/1995 | Stern et al. |
| 5,445,635 A | 8/1995 | Denen |
| 5,451,224 A | 9/1995 | Goble et al. |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,478,303 A | 12/1995 | Foley-Nolan et al. |
| 5,480,399 A | 1/1996 | Hebborn |
| 5,483,952 A | 1/1996 | Aranyi |
| 5,490,850 A | 2/1996 | Ellman et al. |
| 5,496,312 A | 3/1996 | Klicek |
| 5,496,313 A | 3/1996 | Gentelia et al. |
| 5,500,012 A | 3/1996 | Brucker et al. |
| 5,500,616 A | 3/1996 | Ochi |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,681 A | 7/1996 | Strul et al. |
| 5,540,683 A | 7/1996 | Ichikawa |
| 5,540,684 A | 7/1996 | Hassler, Jr. |
| 5,540,724 A | 7/1996 | Cox |
| 5,556,396 A | 9/1996 | Cohen et al. |
| 5,558,671 A | 9/1996 | Yates |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,594,636 A | 1/1997 | Schauder |
| 5,596,466 A | 1/1997 | Ochi |
| 5,599,344 A | 2/1997 | Paterson |
| 5,599,345 A | 2/1997 | Edwards et al. |
| 5,605,150 A | 2/1997 | Radons et al. |
| 5,613,966 A | 3/1997 | Makower et al. |
| 5,613,996 A | 3/1997 | Lindsay |
| 5,625,370 A | 4/1997 | D'Hont |
| 5,626,575 A | 5/1997 | Crenner |
| 5,628,745 A | 5/1997 | Bek |
| 5,643,330 A | 7/1997 | Holsheimer et al. |
| 5,647,869 A | 7/1997 | Goble |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,688,267 A | 11/1997 | Panescu et al. |
| 5,690,692 A | 11/1997 | Fleming |
| 5,693,042 A | 12/1997 | Boiarski et al. |
| 5,694,304 A | 12/1997 | Telefus et al. |
| 5,695,494 A | 12/1997 | Becker |
| 5,696,351 A | 12/1997 | Benn et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,720,744 A | 2/1998 | Eggleston et al. |
| 5,722,975 A | 3/1998 | Edwards et al. |
| 5,733,281 A | 3/1998 | Nardella |
| 5,749,869 A | 5/1998 | Lindenmeier et al. |
| 5,749,871 A | 5/1998 | Hood et al. |
| 5,755,715 A | 5/1998 | Stern |
| 5,766,165 A | 6/1998 | Gentelia et al. |
| 5,769,847 A | 6/1998 | Panescu |
| 5,772,659 A | 6/1998 | Becker et al. |
| 5,792,138 A | 8/1998 | Shipp |
| 5,797,802 A | 8/1998 | Nowak |
| 5,797,902 A | 8/1998 | Netherly |
| 5,814,092 A | 9/1998 | King |
| 5,817,093 A | 10/1998 | Williamson, IV et al. |
| 5,820,568 A | 10/1998 | Willis |
| 5,827,271 A | 10/1998 | Bussey et al. |

| | | | | | | |
|---|---|---|---|---|---|---|
| 5,830,212 | A | 11/1998 | Cartmell | 6,398,781 B1 | 6/2002 | Goble et al. |
| 5,836,943 | A | 11/1998 | Miller, III | 6,402,741 B1 | 6/2002 | Keppel et al. |
| 5,836,990 | A | 11/1998 | Li | 6,402,743 B1 | 6/2002 | Orszulak et al. |
| 5,846,236 | A | 12/1998 | Lindenmeier et al. | 6,436,096 B1 | 8/2002 | Hareyama |
| 5,868,737 | A | 2/1999 | Taylor et al. | 6,451,015 B1 | 9/2002 | Rittman, III et al. |
| 5,868,739 | A | 2/1999 | Lindenmeier et al. | 6,458,121 B1 | 10/2002 | Rosenstock . |
| 5,868,740 | A | 2/1999 | LeVeen et al. | 6,464,689 B1 | 10/2002 | Qin |
| 5,871,481 | A | 2/1999 | Kannenberg et al. | 6,464,696 B1 | 10/2002 | Oyama |
| 5,897,552 | A | 4/1999 | Edwards et al. | 6,506,189 B1 | 1/2003 | Rittman, III et al. |
| 5,908,444 | A | 6/1999 | Azure | 6,508,815 B1 | 1/2003 | Strul |
| 5,913,882 | A | 6/1999 | King | 6,511,476 B2 | 1/2003 | Hareyama |
| 5,921,982 | A | 7/1999 | Lesh et al. | 6,511,478 B1 | 1/2003 | Burnside et al. |
| 5,925,070 | A | 7/1999 | King et al. | 6,524,308 B1 | 2/2003 | Muller et al. |
| 5,931,836 | A | 8/1999 | Hatta et al. | 6,547,786 B1 | 4/2003 | Goble |
| 5,938,690 | A | 8/1999 | Law et al. | 6,562,037 B2 | 5/2003 | Paton |
| 5,948,007 | A | 9/1999 | Starkebaum et al. | 6,565,559 B2 | 5/2003 | Eggleston |
| 5,951,545 | A | 9/1999 | Schilling | 6,573,248 B2 | 6/2003 | Ramasamy et al. |
| 5,951,546 | A | 9/1999 | Lorentzen | 6,575,969 B1 | 6/2003 | Rittman, III et al. |
| 5,954,686 | A | 9/1999 | Garito et al. | 6,620,157 B1 | 9/2003 | Dabney et al. |
| 5,954,717 | A | 9/1999 | Behl et al. | 6,623,423 B2 | 9/2003 | Sakurai |
| 5,954,719 | A | 9/1999 | Chen et al. | 6,635,057 B2 | 10/2003 | Harano |
| 5,961,344 | A | 10/1999 | Rosales et al. | 6,648,883 B2 | 11/2003 | Francischelli |
| 5,971,980 | A | 10/1999 | Sherman | 6,652,514 B2 | 11/2003 | Ellman |
| 5,976,128 | A | 11/1999 | Schilling et al. | 6,663,623 B1 | 12/2003 | Oyama et al. |
| 5,983,141 | A | 11/1999 | Sluijter et al. | 6,663,624 B2 | 12/2003 | Edwards |
| 6,010,499 | A | 1/2000 | Cobb | 6,666,860 B1 | 12/2003 | Takahashi |
| 6,014,581 | A | 1/2000 | Whayne et al. | 6,679,875 B2 | 1/2004 | Honda |
| 6,033,399 | A | 3/2000 | Gines | 6,682,527 B2 | 1/2004 | Strul |
| 6,044,283 | A | 3/2000 | Fein et al. | 6,685,700 B2 | 2/2004 | Behl |
| 6,053,910 | A | 4/2000 | Fleenor | 6,685,701 B2 | 2/2004 | Orszulak et al. |
| 6,053,912 | A | 4/2000 | Panescu et al. | 6,692,489 B1 | 2/2004 | Heim |
| 6,056,745 | A | 5/2000 | Panescu et al. | 6,712,813 B2 | 3/2004 | Ellman |
| 6,056,746 | A | 5/2000 | Goble et al. | 6,730,080 B2 | 5/2004 | Harano |
| 6,063,075 | A | 5/2000 | Mihori | 6,733,495 B1 | 5/2004 | Bek |
| 6,063,078 | A | 5/2000 | Wittkampf | 6,733,498 B2 | 5/2004 | Paton |
| 6,068,627 | A | 5/2000 | Orszulak et al. | 6,740,079 B1 | 5/2004 | Eggers |
| 6,074,386 | A | 6/2000 | Goble et al. | 6,740,085 B2 | 5/2004 | Hareyama |
| 6,093,186 | A | 7/2000 | Goble | 6,783,523 B2 | 8/2004 | Qin |
| RE36,871 | E | 9/2000 | Epstein | 6,790,206 B2 | 9/2004 | Panescu |
| 6,113,591 | A | 9/2000 | Whayne et al. | 6,796,981 B2 | 9/2004 | Wham |
| 6,113,596 | A | 9/2000 | Hooven | 6,824,539 B2 | 11/2004 | Novak |
| 6,123,702 | A | 9/2000 | Swanson et al. | 6,830,569 B2 | 12/2004 | Thompson |
| 6,132,429 | A | 10/2000 | Baker | 6,843,789 B2 | 1/2005 | Goble |
| 6,142,992 | A | 11/2000 | Cheng et al. | 6,849,073 B2 | 2/2005 | Hoey |
| 6,162,217 | A | 12/2000 | Kannenberg et al. | 6,855,141 B2 | 2/2005 | Lovewell |
| 6,171,304 | B1 | 1/2001 | Netherly et al. | 6,855,142 B2 | 2/2005 | Harano |
| 6,203,541 | B1 | 3/2001 | Keppel | 6,860,881 B2 | 3/2005 | Sturm |
| 6,210,403 | B1 * | 4/2001 | Klicek ..................... 606/34 | 6,864,686 B2 | 3/2005 | Novak |
| 6,228,080 | B1 | 5/2001 | Gines | 6,875,210 B2 | 4/2005 | Refior |
| 6,228,081 | B1 | 5/2001 | Goble | 6,893,435 B2 | 5/2005 | Roane |
| 6,231,569 | B1 | 5/2001 | Bek | 7,044,948 B2 | 5/2006 | Keppel |
| 6,235,020 | B1 | 5/2001 | Cheng et al. | 7,060,063 B2 | 6/2006 | Marion et al. |
| 6,238,387 | B1 | 5/2001 | Miller, III | 7,063,692 B2 | 6/2006 | Sakurai et al. |
| 6,238,388 | B1 | 5/2001 | Ellman | 7,066,933 B2 | 6/2006 | Hagg |
| 6,241,725 | B1 | 6/2001 | Cosman | 7,131,860 B2 | 11/2006 | Sartor et al. |
| 6,245,065 | B1 | 6/2001 | Panescu | 7,137,980 B2 | 11/2006 | Buysse et al. |
| 6,246,912 | B1 | 6/2001 | Sluijter et al. | 2001/0014804 A1 | 8/2001 | Goble et al. |
| 6,251,106 | B1 | 6/2001 | Becker et al. | 2001/0031962 A1 | 10/2001 | Eggleston |
| 6,258,085 | B1 | 7/2001 | Eggleston | 2002/0035353 A1 | 3/2002 | Edwards et al. |
| 6,261,285 | B1 | 7/2001 | Novak | 2002/0035363 A1 | 3/2002 | Edwards et al. |
| 6,273,886 | B1 | 8/2001 | Edwards | 2002/0035364 A1 | 3/2002 | Schoenman et al. |
| 6,275,786 | B1 | 8/2001 | Daners | 2002/0068932 A1 | 6/2002 | Edwards |
| 6,293,941 | B1 | 9/2001 | Strul | 2002/0107517 A1 | 8/2002 | Witt et al. |
| 6,306,131 | B1 | 10/2001 | Hareyama et al. | 2002/0111624 A1 | 8/2002 | Witt et al. |
| 6,306,134 | B1 | 10/2001 | Goble et al. | 2002/0193787 A1 | 12/2002 | Qin |
| 6,309,386 | B1 | 10/2001 | Bek | 2003/0004510 A1 | 1/2003 | Wham et al. |
| 6,325,799 | B1 | 12/2001 | Goble | 2003/0060818 A1 | 3/2003 | Kannenberg |
| 6,337,998 | B1 | 1/2002 | Behl et al. | 2003/0078572 A1 | 4/2003 | Pearson et al. |
| 6,338,657 | B1 | 1/2002 | Harper et al. | 2003/0139741 A1 | 7/2003 | Goble et al. |
| 6,350,262 | B1 | 2/2002 | Ashley | 2003/0153908 A1 | 8/2003 | Goble |
| 6,358,245 | B1 | 3/2002 | Edwards | 2003/0163123 A1 | 8/2003 | Goble |
| 6,383,183 | B1 | 5/2002 | Sekino et al. | 2003/0163124 A1 | 8/2003 | Goble |
| 6,398,779 | B1 | 6/2002 | Buysse et al. | 2003/0171745 A1 | 9/2003 | Francischelli |

| | | | | | | |
|---|---|---|---|---|---|---|
| 2003/0199863 | A1 | 10/2003 | Swanson | DE | 19717411 | 11/1998 |
| 2003/0225401 | A1 | 12/2003 | Eggers et al. | DE | 19848540 A1 | 5/2000 |
| 2004/0002745 | A1 | 1/2004 | Flemming | EP | 246350 | 11/1987 |
| 2004/0015163 | A1 | 1/2004 | Buysse et al. | EP | 310431 | 4/1989 |
| 2004/0015216 | A1 | 1/2004 | DeSisto | EP | 325456 | 7/1989 |
| 2004/0019347 | A1 | 1/2004 | Sakurai | EP | 336742 | 10/1989 |
| 2004/0024395 | A1 | 2/2004 | Ellman | EP | 390937 | 10/1990 |
| 2004/0030328 | A1 | 2/2004 | Eggers | EP | 556705 | 8/1993 |
| 2004/0030330 | A1 | 2/2004 | Brassell et al. | EP | 0569130 A1 | 11/1993 |
| 2004/0044339 | A1 | 3/2004 | Beller | EP | 608609 | 8/1994 |
| 2004/0049179 | A1 | 3/2004 | Francischelli | EP | 836868 | 4/1998 |
| 2004/0054365 | A1 | 3/2004 | Goble | EP | 878169 | 11/1998 |
| 2004/0059323 | A1 | 3/2004 | Sturm et al. | EP | 1293171 | 3/2003 |
| 2004/0068304 | A1 | 4/2004 | Paton | EP | 0880220 B1 | 6/2006 |
| 2004/0082946 | A1 | 4/2004 | Malis | FR | 1275415 | 10/1961 |
| 2004/0095100 | A1 | 5/2004 | Thompson | FR | 1347865 | 11/1963 |
| 2004/0097912 | A1 | 5/2004 | Gonnering | FR | 2313708 | 12/1976 |
| 2004/0097914 | A1 | 5/2004 | Pantera | FR | 2502935 | 10/1982 |
| 2004/0097915 | A1 | 5/2004 | Refior | FR | 2517953 | 6/1983 |
| 2004/0116919 | A1 | 6/2004 | Heim | FR | 2573301 | 5/1986 |
| 2004/0133189 | A1 | 7/2004 | Sakurai | GB | 607850 | 9/1948 |
| 2004/0138653 | A1 | 7/2004 | Dabney | GB | 855459 | 11/1960 |
| 2004/0138654 | A1 | 7/2004 | Goble | GB | 902775 | 8/1962 |
| 2004/0147918 | A1 | 7/2004 | Keppel | GB | 2164473 | 3/1986 |
| 2004/0167508 | A1 | 8/2004 | Wham et al. | GB | 2214430 | 9/1989 |
| 2004/0172016 | A1 | 9/2004 | Bek | GB | 2358934 A | 8/2001 |
| 2004/0193148 | A1 | 9/2004 | Wham et al. | SU | 166452 | 1/1965 |
| 2004/0230189 | A1 | 11/2004 | Keppel | SU | 727201 | 4/1980 |
| 2004/0243120 | A1 | 12/2004 | Orszulak et al. | WO | WO92/06642 | 4/1992 |
| 2004/0260279 | A1 | 12/2004 | Goble | WO | WO93/24066 | 12/1993 |
| 2005/0004564 | A1 | 1/2005 | Wham | WO | WO94/24949 | 11/1994 |
| 2005/0004569 | A1 | 1/2005 | Witt et al. | WO | WO94/28809 | 12/1994 |
| 2005/0021022 | A1 | 1/2005 | Sturm et al. | WO | WO95/09577 | 4/1995 |
| 2005/0101951 | A1 | 5/2005 | Wham | WO | WO95/19148 | 7/1995 |
| 2005/0113818 | A1 | 5/2005 | Sartor | WO | WO96/02180 | 2/1996 |
| 2005/0113819 | A1 | 5/2005 | Wham | WO | WO96/04860 | 2/1996 |
| 2005/0149151 | A1 | 7/2005 | Orszulak | WO | WO96/08794 | 3/1996 |
| 2005/0182398 | A1 | 8/2005 | Paterson | WO | WO96/18349 | 6/1996 |
| 2005/0197659 | A1 | 9/2005 | Bahney | WO | WO96/29946 | 10/1996 |
| 2005/0203504 | A1 | 9/2005 | Wham et al. | WO | WO96/39914 | 12/1996 |
| 2006/0025760 | A1 | 2/2006 | Podhajsky | WO | WO97/06739 | 2/1997 |
| 2006/0079871 | A1 | 4/2006 | Plaven et al. | WO | WO97/06740 | 2/1997 |
| 2006/0161148 | A1 | 7/2006 | Behnke | WO | WO97/06855 | 2/1997 |
| 2006/0178664 | A1 | 8/2006 | Keppel | WO | WO97/17029 | 5/1997 |
| 2006/0224152 | A1 | 10/2006 | Behnke et al. | WO | WO02/011634 | 2/2002 |
| 2006/0281360 | A1 | 12/2006 | Sartor et al. | WO | WO02/045589 | 6/2002 |
| | | | | WO | WO02/47565 | 6/2002 |
| | | | | WO | WO02/088128 | 7/2002 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3143421 | 8/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 A1 | 5/1995 |

| | | |
|---|---|---|
| WO | WO 03/092520 | 11/2003 |
| WO | WO 05/060365 | 11/2003 |
| WO | WO 04/028385 | 4/2004 |
| WO | WO 04/098385 | 4/2004 |
| WO | WO 05/046496 | 5/2005 |
| WO | WO 05/048809 | 6/2005 |
| WO | WO 05/050151 | 6/2005 |
| WO | WO05048809 A1 | 6/2005 |

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Anderson et al., "A Numerical Study of Rapid Heating for High Temperature Radio Frequency Hyperthermia" International Journal of Bio-Medical Computing, 35 (1994) pp. 297-307.

Astrahan, "A Localized Current Field Hyperthermia System for Use with 192-Iridium Interstitial Implants" Medical Physics, 9 (3), May/Jun. 1982.

Bergdahl et al., "Studies on Coagulation and the Development of an Automatic computerized Bipolar Coagulator" Journal of Neurosurgery 75:1, (Jul. 1991) pp. 148-151.

Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. Ml, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2. No. 5, pp. 399-404.
Sugita et al., "Bipolar Coagulator with Automatic Thermocontrol" J. Neurosurg., vol. 41, Dec. 1944, pp. 777-779.
Vallfors et al., "Automatically Controlled Bipolar Electrosoagulation-'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Kevin Banks, "The Goertzel Algorithm" Embedded Systems Programming, Aug. 28, 2002.
Medtrex Brochure "The O.R. Pro 300" 1 p. Sep. 1998.
Valleylab Brochure "Valleylab Electroshield Monitoring System" 2 pp. Nov. 1995.
Richard Wolf Medical Instruments Corp. Brochure, "Kleppinger Bipolar Forceps & Bipolar Generator" 3 pp. Jan. 1989.
Bergdahl et al. "Studies on Coagulation and the Development of an Automatic Computerized Bipolar Coagulator" J.Neurosurg, vol. 75, Jul. 1991, pp. 148-151.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
Valleylab Brochure Valleylab Electroshield Monitoring System 2 pp. Nov. 1995.
Richard Wolf Medical Instruments Corp. Brochure, "Kleppinger Bipolar Forceps & Bipolar Generator" 3 pp. Jan. 1989.
Chicharo et al. "A Sliding Goertzel Algorith" Aug. 1996, pp. 283-297 Signal Processing, Elsevier Science Publishers B.V. Amsterdam, NL vol. 52 No. 3.
Ogden Goertzel Alternative to the Fourier Transform: Jun. 1993 pp. 485-487 Electronics World; Reed Business Publishing, Sutton, Surrey, BG vol. 99, No. 9. 1687.
International Search Report EP 0409964 Jul. 13, 2004.
International Search Report—PCT/US03/37110, Jul. 2005.
International Search Report—PCT/US03/37310, Aug. 2004.
International Search Report—EP4009964, Jul. 2004.
International Search Report—EP98300964.8, Dec. 2000.
International Search Report—EP04015981.6, Oct. 2004.
Chicharo et al. "A Sliding Goertzel Algorith" Aug. 1996, pp. 283-297 Signal Processing, Elsevier Science Publishers B.V. Amsterdam, NL vol. 52 No. 3.
Ogden "Goertzel Alternative to the Fourier Transform: Jun. 1993 pp. 485-487 Electronics World; Reed Business Publishing, Sutton, Surrey, BG vol. 99, No. 9. 1687.
Ogden "Goertzel Alternative to the Fourier Transform" Jun. 1993 pp. 485-487 Electronics World; Reed Business Publishing, Sutton, Surrey, GB vol. 99, No. 1687.
International Search Report EP 06000708.5 dated Apr. 21, 2006.
International Search Report-Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . ." Journal of Applied Sciences-Yingyong Kexue Xuebao, Shanghai CN, vol. 23 No. 2; (2005-03); 160-164.

* cited by examiner

FIG. 1

AUTOMATIC CONTROL SYSTEM FOR AN ELECTROSURGICAL GENERATOR

CROSS REFERENCE TO RELATED APPLICATIONS:

This application claims the benefit of U.S. Provisional Application No. 60/515,816, filed Oct. 30, 2003.

BACKGROUND OF THE INVENTION

1. Technical Field

The present disclosure relates to electrosurgery. More particularly, the present disclosure relates to an automatic control system for an electrosurgical generator.

2. Background of Related Art

Surgeons have tried to deal with energy application by adjusting the basic power level of the electrosurgical generator and using a hand or foot switch to control the power applied over time. Unfortunately, that technique often leads to unintended power delivery or undesired duration of power delivery to the surgical site. Surgeons also experience difficulty in repeatably and/or consistently desiccating tissue to the desired levels due to the user's reaction time and/or machine response time when manual or foot activated switches are used for manual control. In addition, during endoscopic procedures, visual and tactile feedback is diminished.

A circuit for automatically controlling the output of an electrosurgical generator is disclosed in U.S. Pat. No. 6,210,403 to Klicek, currently owned, and assigned to Sherwood Services AG, the contents of which are hereby incorporated by reference in its entirety. U.S. Pat. No. 6,210,403 relates to an electrosurgical generator control, which is responsive to the tissue impedance between the active and return electrodes during desiccation.

A method for tone detection using the Goertzel algorithm is disclosed in an article entitled *The Goertzel Algorithm* by Kevin Banks (*The Goertzel Algorithm* by Kevin Banks, <http://www.embedded.com/showArticle.jhtml?articleID=9900772>, last visited on Jul. 24, 2003). The Banks' article relates to using a modified Goertzel algorithm for determining whether a tone of a specific frequency is present. The Goertzel algorithm calculates both the magnitude and the phase of signal at a specific frequency and is functionally equivalent to performing a Discrete Fourier Transform (DFT) at a single frequency, but is much less computationally demanding. The DFT is a method for calculating the magnitude and phase of a band of frequencies of interest. An N-point DFT is computationally demanding, but will calculate the real and imaginary frequency terms for all the frequencies up to half the sampling rate of the signal.

According to Banks, using a modified Goertzel algorithm is preferable in applications requiring tone detection such as DTMF, call progress decoding, and frequency response measurements. However, the modified Goertzel algorithm proposed by Banks does not provide the real and imaginary frequency components of the sampled waveform. As a result, the modified Goertzel algorithm is unsuited for determining the phase of the waveform.

It is an object of the present disclosure to provide an automatic control system that uses fewer computational steps.

Another object of the present disclosure is to provide an automatic control system that measures the power delivered to a patient.

Yet a further object of the present disclosure is to provide an automatic control system that is adaptable to both monopolar and bipolar electrosurgical generator configurations.

It is a further object of the present disclosure to provide an automatic control system that adjusts the power delivered to a patient by an electrosurgical generator.

SUMMARY

An automatic control system for an electrosurgical generator is hereinafter disclosed. The automatic control system includes voltage and current sensing circuits, a processing circuit, an output determining circuit, and a control circuit. The voltage and current sensing circuits produce voltage and current signals that are representative of the voltage and current present in the output of the electrosurgical generator. These signals are coupled to the processing circuit that uses a Goertzel algorithm to determine the phase difference between the voltage waveform and the current waveform according to circuitry within the processing circuit.

The processing circuit produces a phase difference signal that is communicated to the output determining circuit for determining the output of the electrosurgical generator. The output determining circuit produces an output signal that is compared to a reference signal in the control circuit. The control circuit determines the difference between the output signal and the reference signal and generates a feedback signal that is representative of the difference. The feedback signal is communicated to a drive control circuit for controlling the output of a drive circuit.

Preferably, the Goertzel algorithm determines phase angle between the voltage waveform and the current waveform. Advantageously, the phase angle is used to compensate for energy delivery at the operating site. It is also contemplated that the phase angle can be utilized to provide feedback to the generator about tissue relating to at least one of: tissue change over time, tissue impedance, tissue type, tissue cycle completion.

BRIEF DESCRIPTION OF THE DRAWINGS

Embodiments of the presently disclosed are described herein with reference to the drawing, wherein.

DETAILED DESCRIPTION

Figure 1:
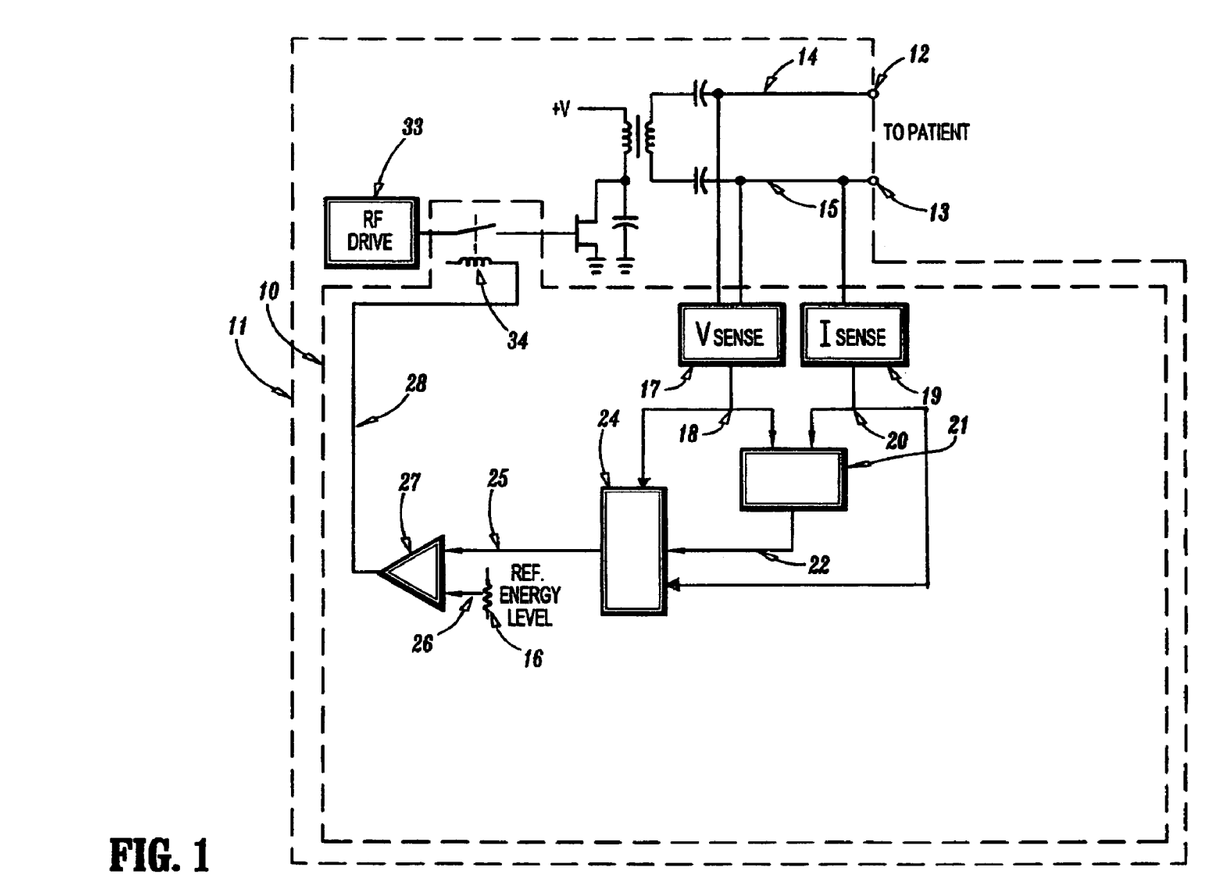
FIG. 1 is block diagram of an automatic control system for an electrosurgical generator in accordance with an embodiment of the present disclosure.

Embodiments of the presently disclosed automatic control system will now be described in detail with reference to the drawing where, in FIG. 1, an exemplary embodiment of the presently disclosed automatic control system 10 is illustrated. Automatic control system 10 is ideally disposed within an electrosurgical generator 11. Electrosurgical generator 11 includes a user control 16 preferably on its front panel accessible to the doctor for setting the output level desired for a particular electrosurgical procedure. User control 16 may be a knob, a slider, or other structures and/or devices as is known in the art for use by the doctor to set a reference signal 26 indicative of the desired output.

A voltage sensing circuit 17 has an isolation transformer, which acts as an inductive pickup. Its primary side is electrically connected between leads 14 and 15 for inducing a voltage signal 18 on the secondary windings thereby responding to the high frequency electrosurgical energy supplied by electrosurgical generator 11 flowing through leads 14 and 15. A current sensing circuit 19 responds to high frequency electrosurgical energy supplied by electrosurgical generator 11 and flowing through return lead 15. Current sensing circuit 19 provides a current signal 20 as an instantaneous output representative of the current passing therethrough. Preferably, voltage signal 18 and current signal 20 are AC waveforms that are representative of the output of leads 14 and 15.

Operatively connected to leads 14 and 15 are electrodes 12 and 13. Electrodes 12 and 13 are used to provide the output of electrosurgical generator 11 to a patient. In a bipolar configuration, electrodes 12 and 13 are both present in an electrosurgical instrument (not shown), which is used at a surgical site of the patient with electrode 13 providing the return path for the output of electrosurgical generator 11.

In a monopolar configuration, the electrosurgical instrument (not shown) includes one electrode 12 while electrode 13 is connected to a surface near the patient and provides the return path. The active ends of electrodes 12 and 13 are electrically connected to electrosurgical generator 11 by one or more conductive cables. Although monopolar and bipolar configurations are used in electrosurgical generators, they are electrically equivalent and equally suited for use with automatic control system 10 of the present disclosure.

Voltage sensing circuit 17 and current sensing circuit 19 are operatively coupled to a processing circuit 21. In a preferred embodiment, processing circuit 21 includes one or more digital signal processors (DSP) and associated circuitry. The DSPs may be upgradeable using flash ROM as is known in the art. Upgrades for the DSPs may be stored on computer readable media such as magnetic disks, optical disks, magnetic tape, or other media as is known in the art. Processing circuit 21 simultaneously receives voltage signal 18 and current signal 20.

In a preferred embodiment, processing circuit uses the Goertzel algorithm for processing voltage and current signals 18, 20. The Goertzel algorithm is advantageously implemented as a second order recursive infinite impulse response filter, as shown below.

The Goertzel algorithm is defined by the equation:

$$Hf_i(z) = \frac{1 - e^{\frac{2\pi f_i}{f_s}} z^{-1}}{1 - 2\cos\left(\frac{2\pi f_i}{f_s}\right) z^{-1} + z^{-2}}$$

Where $f_i$ is the frequency of interest and $f_A$ is the sampling frequency.

Second Order Recursive Goertzel Filter

The Goertzel algorithm is implemented digitally as:

$$v_k[n] = x[n] + 2\cos\left(\frac{2\pi k}{N}\right) v_k[n-1] - v_k[n-2]$$

Since the output frequency of electrosurgical generator 11 is known, and preferably, about 470 KHz, the digitally implemented Goertzel algorithm calculates the real and imaginary frequency components of the known waveform using the following formulae:

Real=$(v_k[n-1]-(v_k[n-2]*\cos(2\pi k/N))$

Imaginary=$(v_k[n-2]*\sin(2\pi k/N))$

Magnitude=square_root (Real$^2$+Imaginary$^2$)

Phase=ATAN (Imaginary/Real)

The DSPs of processing circuit 21 calculates the Voltage_Phase for voltage signal 18 and the Current_Phase for current signal 20 according to the above-mentioned formulae. Additionally, the phase shift, preferably in radians, between voltage signal 18 and current signal 20 can then be calculated by applying the algorithm on voltage signal 18 and current signal 20 concurrently and subtracting the difference in the phases as follows:

Phase_Difference=Current_Phase−Voltage_Phase.

This phase calculation is implemented to calculate the phase differential between voltage signal 18 and current signal 20. In the preferred embodiment, the DSPs of processing circuit 21 include the Goertzel algorithm along with associated processing software to determine the phase difference between voltage signal 18 and current signal 20. Additionally, processing circuit 21 determines a magnitude value of both voltage and current signals 18, 20 and communicates these values along with the Phase_Difference to an output determining circuit 24 as phase difference signal 22.

In one embodiment, output determining circuit 24 includes a microprocessor with associated circuitry for calculating the dosage (current, power or voltage) output of electrosurgical generator 11 using the calculated Phase_Difference and values of the voltage and current outputs of electrosurgical generator 11. In an AC circuit, power is determined by the formula P=EI cos (q), where P is the power measured in watts, E is a voltage value, I is a current value, and q is the Phase_Difference between the voltage and current waveforms.

By advantageously using the Goertzel algorithm for a single known value of frequency, automatic control system 10 of the present disclosure calculates the output for electrosurgical generator 11 using fewer computational steps than a DFT. More particularly, due to the frequency of the output and the selected sampling rate for the voltage and current components of the output, there is insufficient bandwidth to use a DFT to determine the Phase_Difference. However, processing circuit 21, according to the present disclosure, determines the Phase_Difference using the Goertzel algorithm, thereby using fewer computational steps and within the existing bandwidth. As used herein, bandwidth refers to the time between the voltage and/or current samples acquired by voltage and current sensing circuits 17, 19.

Preferably, automatic control system 10 additionally calculates the output of electrosurgical generator 11 and performs any necessary adjustments to the output within the existing bandwidth. In the preferred embodiment, after automatic control system 10 calculates the output and performs any necessary adjustments, there is additional bandwidth available before the next sample of the output is taken. Furthermore, by using fewer computational steps to determine Phase_Difference, a minimum amount of data is lost between samples.

Preferably, the Goertzel algorithm is used to determine the phase angle or Phase_Difference between the voltage waveform and the current waveform. Advantageously, the Phase_Difference is used to compensate for energy delivery at the operating site. It is also contemplated that the Phase_Difference can be utilized to provide feedback to the generator 11 about tissue relating to at least one of: tissue change over time, tissue impedance, tissue type, tissue cycle completion.

Extra bandwidth between samples of the output is advantageously utilized to perform additional calculations, perform additional control functions, or allow the output frequency of electrosurgical generator 11 to be increased. By way of example, such additional calculations include average values of voltage and current, peak values of voltage and current, and root mean square values of voltage and current. It is contemplated that, additional control functions may include calibration of system components and adjusting system parameters for cable compensation.

Output determining circuit 24 includes circuitry for determining electrosurgical generator's 11 output. Preferably, output determining circuit 24 includes a processor and associated circuitry for determining the current, voltage, and/or power delivered to the patient. An output signal 25 is generated by output determining circuit 24 and is coupled to an input of a control circuit 27. In a preferred embodiment, voltage and current signals 18, 20 are also communicated to output determining circuit 24. The circuitry in output determining circuit 24 determines the output of electrosurgical generator 11 using voltage and current signals 18, 20 in conjunction with phase difference signal 22. The output of electrosurgical generator 11 is represented by a value of output signal 25.

Control circuit 27 has at least two inputs where a first input is output signal 25 and a second input is a reference signal 26. Reference signal 26 is controlled by the setting of user control 16 and it establishes a reference value for control circuit 27. In a preferred embodiment, control circuit 27 includes at least one DSP and associated circuitry for determining the difference between output signal 25 and reference signal 26. A feedback signal 28 is generated by control circuit 27 where the feedback signal 28 is representative of the difference between output signal 25 and reference signal 26.

Feedback signal 28 is operatively coupled to a drive control circuit 34 for controlling the output of a drive circuit 33. Drive control circuit 34 includes structure and/or circuitry for controlling the output of drive circuit 33. In one embodiment, drive control circuit 34 controls an input to drive circuit 33 for adjusting the output of drive circuit 33 according to a value of feedback signal 28. Alternatively, drive control circuit 34 controls the output of drive circuit 33 by adjusting the biasing of associated circuitry in drive circuit 33 according to a value of feedback signal 28, thereby controlling its output.

During operation of electrosurgical generator 11, drive circuit 33 produces an output, or drive signal, that is coupled to a first winding of a transformer. A portion of the output present on the first winding of the transformer is coupled to a second winding of the transformer that is electrically communicated to leads 14 and 15. Leads 14 and 15 are electrically connected to electrodes 12 and 13 for operating an electrosurgical instrument (not shown) during an electrosurgical procedure. The output present on leads 14 and 15 is sampled by voltage sensing circuit 17 and current sensing circuit 19. As discussed in detail above, the Phase_Difference between the output voltage waveform and output current waveform is determined by processing circuit 21 and the output of electrosurgical generator 11 is determined by output determining circuit 24.

As output from electrosurgical generator 11 increases, the values of voltage signal 18 and current signal 20 also increase in a proportional relationship. Output determining circuit 24 receives phase difference signal 22 from processing circuit 21 and determines the change in the output. Accordingly, an increase in output is reflected in an increase in output signal 25 that is coupled to control circuit 27. Due to the increase in output signal 25, the difference between output signal 25 and reference signal 26 decreases resulting in a decreased feedback signal 28.

When output signal 25 is substantially equal to reference signal 26, feedback signal 28 is essentially zero. Additionally, the substantial equality of these signals indicates that electrosurgical generator 11 is producing the desired output for the selected electrosurgical procedure.

Other uses for electrosurgical generator 11 including automatic control system 10 are envisioned to be within the scope of this disclosure. Such applications include procedures where fine control and accuracy of delivered output is desirable. These applications include neurosurgical applications, ligasure sealing, thoracic and throat procedures, ocular surgery, procedures on small structures, and neonatal procedures. The determination of the Phase_Difference will allow output compensation so that with a known cable and handset, the output delivered to the patient can be more accurately calculated.

Further still, since automatic control system 10 determines the Phase_Difference between the voltage and current components of the output, this information may be coupled with known values of a handset and cable electrical characteristics (i.e. resistance, capacitance, and inductance) to determine the distance between the electrosurgical instrument and the surface of the patient. This is especially advantageous in a coagulation procedure where an electrosurgical generator is used in conjunction with an electrosurgical pencil (i.e. monopolar mode of operation) disposede above the surface of the patient. In this procedure, the electrosurgical generator typically produces a high voltage that arcs from the electrosurgical pencil to the surface of the patient, thereby coagulating affected tissue. By determining the distance between the electrosurgical pencil and the patient, automatic control system 10 can adjust the power output to a desired value that is sufficient to coagulate the affected tissue without producing additional power.

From the foregoing and with reference to the various figure drawings, those skilled in the art will appreciate that certain modifications can also be made to the present disclosure without departing from the scope of the same. For example, Although a Goertzel algorithm is described herein as one low computation algorithm for determining the magnitude and phase components of a narrow band sinusoidal signal, any other algorithm which similarly derives the magnitude and phase components could also be used, such as a 'Fourier Transform', 'Fast Fourier Transform (FFT)' or 'Discrete Fourier Transform (DFT)'. Other similar algorithms which focus on a narrow band of frequencies, will gain the benefit of reduced computational effort similar to the Goertzel implementation.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. A system for controlling an output of an electrosurgical generator comprising:
   a drive circuit for generating an output, the output being responsive to a feedback signal and operatively coupled to at least one electrode of the electrosurgical generator;
   at least one sensing circuit operatively coupled to the at least one electrode for generating a first signal corresponding to a value of a voltage waveform present on the at least one electrode and a second signal corresponding to a value of a current waveform present on the at least one electrode;
   a processing circuit for receiving the first and second signals, wherein the processing circuit implements the Goertzel algorithm for determining a phase of each of the voltage waveform and the current waveform;
   a determining circuit in communication with the processing circuit for generating an output signal as a function of a phase difference between the voltage waveform and the current waveform; and
   a control circuit for generating a feedback signal, the feedback signal representative of a difference between a value of the output signal and a reference value, the feedback signal operatively coupled to the drive circuit.

2. The system of claim 1, wherein the processing circuit includes at least one digital signal processor.

3. The system of claim 1, wherein the phase difference is used to compensate for energy delivery at the operating site.

4. The system of claim 1, wherein the phase difference provides feedback to the generator about tissue relating to at least one of: tissue change over time, tissue impedance, tissue type, tissue cycle completion.

5. The system of claim 1, wherein the at least one sensing circuit includes a voltage sensing circuit and/or a current sensing circuit.

6. A system for controlling an output of an electrosurgical generator comprising:
   a drive circuit for generating an output, the output being responsive to a feedback signal from at least one electrode operatively coupled to the electrosurgical generator;
   at least one sensing circuit operatively coupled to the at least one electrode that generates a first signal corresponding to a value of a voltage waveform present on the at least one electrode and a second signal corresponding to a value of a current waveform present on the at least one electrode;
   a processing circuit that receives the first and second signals, wherein the processing circuit implements the Goertzel algorithm for determining a phase of each of the voltage waveform and the current waveform; and
   a determining circuit in communication with the processing circuit that generates an output signal as a function of a phase difference between the voltage waveform and the current waveform.

7. The system of claim 6, further comprising:
   a control circuit that generates a feedback signal, the feedback signal representative of a difference between a value of the output signal and a reference value, the feedback signal operatively coupled to the drive circuit.

8. The system of claim 6, wherein the processing circuit includes at least one digital signal processor.

9. The system of claim 6, wherein the phase difference is used to compensate for energy delivery at the operating site.

10. The system of claim 6, wherein the phase difference provides feedback to the generator relating to at least one of: tissue change over time, tissue impedance, tissue type and tissue cycle completion.

11. The system of claim 6, wherein the at least one sensing circuit includes at least one of a voltage sensing circuit and a current sensing circuit.

12. A method for controlling an output of an electrosurgical generator comprising the step of:
   generating an output through at least one electrode operatively coupled to the electrosurgical generator, the output being responsive to a feedback signal;
   generating a first signal corresponding to a value of a voltage waveform present on the at least one electrode and a second signal corresponding to a value of a current waveform present on the at least one electrode;
   processing the first and second signals using the Goertzel algorithm to determine a phase of each of the voltage waveform and the current waveform; and
   generating an output signal as a function of a phase difference between the voltage waveform and the current waveform.

13. A method according to claim 12, further comprising the step of:
   generating a feedback signal representative of a difference between a value of the output signal and a reference value, the feedback signal operatively coupled to the drive circuit.

* * * * *